United States Patent
Porssa et al.

(10) Patent No.: US 6,251,964 B1
(45) Date of Patent: Jun. 26, 2001

(54) BIOCOMPATIBLE COMPOSITIONS

(75) Inventors: Manuchehr Porssa; Paul Matthew McNeillis; Richard Neil Templar Freeman, all of Surrey (GB)

(73) Assignee: Biocompatibles Limited, Surrey (GB)

( * ) Notice: Subject to any disclaimer, the term of this patent is extended or adjusted under 35 U.S.C. 154(b) by 0 days.

(21) Appl. No.: 09/117,729

(22) PCT Filed: Nov. 20, 1997

(86) PCT No.: PCT/GB97/03189

§ 371 Date: Aug. 5, 1998

§ 102(e) Date: Aug. 5, 1998

(87) PCT Pub. No.: WO98/22516

PCT Pub. Date: May 28, 1998

(30) Foreign Application Priority Data

Nov. 20, 1996 (GB) .................................................. 9624130

(51) Int. Cl.⁷ ....................... A61K 31/715; C08L 101/04; C08L 101/06; C08L 5/04; C08L 5/10
(52) U.S. Cl. ........................... 523/105; 523/331; 523/112; 524/27; 524/28; 524/547; 526/277
(58) Field of Search ..................................... 523/105, 331, 523/112; 524/547, 27, 28; 526/277

(56) References Cited

U.S. PATENT DOCUMENTS

| 3,634,123 | 1/1972 | Eriksson . |
| 3,861,948 | 1/1975 | Samour et al. . |
| 5,342,621 | 8/1994 | Eury . |
| 5,712,326 | * 1/1998 | Jones et al. .......................... 524/547 |

FOREIGN PATENT DOCUMENTS

| 0086186 | 8/1983 | (EP) . |
| 0086187 | 8/1983 | (EP) . |
| 0350161 | 1/1990 | (EP) . |
| 7-184989 | 7/1995 | (JP) . |
| WO 9207885 | 5/1992 | (WO) . |
| WO 9301221 | 1/1993 | (WO) . |
| WO 9321970 | 11/1993 | (WO) . |

OTHER PUBLICATIONS

U.S. Ser. No. 09/003,470, N/A.*
U.S. Ser. No. 09/341,476, N/A.*

* cited by examiner

Primary Examiner—Peter A. Szekely
(74) Attorney, Agent, or Firm—Sughrue, Mion, Zinn, Macpeak & Seas, PLLC

(57) ABSTRACT

A polymer is formed from monomers including a zwitterionic monomer, a cationic monomer and a hydrophobic termonomer. The polymer may be cross-linkable. The polymer may be coated onto a surface from a liquid coating composition followed by contacting the coated surface with heparin. The double coated substrates have improved heparin activity over extended periods as compared to heparinised surfaces which are commercially available. Other anionically charged mucopolysaccharides may be used. The polymers may also scavenge heparin from treated blood to avoid use of potentially toxic heparin inhibitors. Preferably the terpolymer is formed from 2-methacryloyloxyethyl-2-(trimethylamonium)phosphate inner salt, choline methacrylate and n-dodecyl methacrylate.

25 Claims, No Drawings

BIOCOMPATIBLE COMPOSITIONS

The present invention relates to novel biocompatible polymers, the use of these polymers to improve binding of mucopolysaccharides to substrates to improve their hemocompatibility and compositions containing mucopolysaccharides and the polymer.

In WO-A-93/01221 we describe various polymers and their use to coat surfaces to improve their biocompatibility. The polymers include zwitterionic groups and pendant groups which are capable of providing stable surface binding of the polymer to underlying substrate surfaces. The binding may be by provision of pendant hydrophobic groups which physisorb onto hydrophobic substrates, by counterionic attraction between pendant ionic groups on the polymer and oppositely charged groups at the substrate surface, by providing covalent attachment between coreactive pendant groups on the polymer and groups at the substrate surface or by crosslinking the polymer after coating. Post coating crosslinking may also be used to improve the stability of a polymer which is physisorbed, covalently bonded or counterionically bonded to the surface. The polymers have good hemocompatibility as indicated by the low platelet adhesion values reported in that specification.

It has also been shown that zwitterionic groups at substrate surfaces, for instance of contact lenses, show lower rates of deposition of proteins and lipids from biological liquids such as tear film. In WO-A-92/07885, reduced levels of protein deposition are described for contact lenses formed from a hydrogel of a crosslinked copolymer of copolymerisable zwitterionic monomer and non ionic comonomer.

In WO-A-93/21970 it is disclosed that microorganisms, especially bacteria, adhere to surfaces having pendant phosphoryl choline groups than to similar surfaces without such groups present.

Another way of reducing the thrombogenicity of surfaces has involved attachment or adsorption of anti-thrombogenic active compounds to substrate surfaces. For instance heparin may be attached through covalent or counterionic bonding to surfaces. In U.S. Pat. No. 3,634,123 the binding of heparin to a surface was increased by incorporation of cationic surfactant. A related process is described in EP-A-0350161, in which a surface is first coated with a cationic surfactant and subsequently with heparin. In EP-A-0086187 the surface is first coated with a cationic polymer and subsequently with heparin. In JP-A-53/137268 a cross-linked acrylic copolymer of a cationic monomer and a polyethyleneglycol monomer is blended with polyurethane and made into tubing which can be coated with heparin. In EP-A-0086186 heparin is attached to an underlying surface through a covalent bond via the end carbohydrate unit. In U.S. Pat. No. 5,342,621, a complex is formed of heparin with phosphatidyl choline and admixed with a polymer of caprolactone or L-lactic acid (both substantially unchanged overall) and subsequently used to coat medical devices.

The present inventors have discovered that the performance of heparin coated devices which are commercially available, for instance as components of extra corporeal devices, deteriorates after short periods of use, for instance half an hour. It is not known whether this is due to the heparin being removed from the surface or due to the surface becoming fouled by components of blood or other biological liquid in contact with the surface during use such that the heparin is masked. The present invention seeks to provide a substrate surface which is hemocompatible and retains its hemocompatible properties over longer term in use.

Generally patients who are undergoing complex operations requiring that their blood be directed through extra corporeal circuitry, require administration of heparin into the circulation to prevent the blood clotting. Subsequently the heparin has to be neutralised or removed from the blood stream. In order to remove heparin from the circulation without administering a further active compound to neutralise the heparin, it has been suggested to immobilise protamine, a cationic polypeptide used to neutralise heparin, at the surfaces of a filter used in an extra corporeal blood circuit, to scavenge heparin from a patient systemically heparinised.

In U.S. Pat. No. 3,861,948 pressure sensitive adhesives are copolymers of ionic monomer and alkylacrylate monomers. The ionic monomers may be cationic and/or zwitterionic. Zwitterionic monomers are sulpho or carboxybetaines, and are used in combination with permanent cationic monomers and monomers with glycidyl groups which can be reacted after coating to cross-link the polymer.

A new terpolymer according to the invention has an overall cationic charge and is formed from ethylenically unsaturated monomers including a) a zwitterionic monomer of the formula I $$YBX \qquad\qquad I$$

wherein

B is a bond or a straight or branched alkylene, alkylene-oxa-alkylene or alkylene-oligooxa-alkylene group, any of which optionally include one or more fluorine substituents;

X is an organic group having a zwitterionic moiety; and

Y is an ethylenically unsaturated polymerisable group;

b) a cationic monomer of the formula II $$Y^1B^1Q^1 \qquad\qquad II$$

wherein $B^1$ is a bond or a straight or branched alkylene, alkylene-oxa-alkylene or alkylene-oligooxa-alkylene group, any of which optionally includes one or more fluorine substituents;

$Y^1$ is an ethylenically unsaturated polymerisable group; and

Q is an organic group having a cationic or cationisable moiety; and c) a termonomer of the formula III $$Y^2B^2Q^2 \qquad\qquad III$$

wherein $B^2$ is a bond or a straight or branched alkylene, alkylene-oxa-alkylene or alkylene-oligooxa-alkylene group, any of which may optionally include one or more fluorine substituents;

$Y^2$ is an ethylenically unsaturated polymerisable group; and $Q^2$ is an organic group having a hydrophobic group selected from alkyl groups having at least six carbon atoms, fluorine substituted alkyl groups and alkyl groups having at least one siloxane substituent.

The terpolymer may include pendant groups capable of providing covalent bonding at the substrate surface or crosslinking between polymer chains. Such groups are generally introduced by incorporation of additional reactive monomers into the monomer mixture. A termonomer may, for instance, comprise a covalent reactive group which is capable of forming a covalent bond with coreactive groups at the substrate surface. Alternatively the copolymer may be crosslinked after coating by subjecting a polymer having pendant crosslinkable groups to conditions such that crosslinking takes place.

A covalent reactive monomer may have the general formula IV:

$$Y^3B^3Q^3 \qquad\qquad \text{IV}$$

wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group; and $Q^3$ is an organic group having a reactive group capable, on imposition of an external stimulus, of reacting with a coreactive group on the surface of a substrate or which is pendant on the polymer.

Reactive groups $Q^3$ may also provide crosslinkability on the polymer. For instance such groups may react with each other or may react with different coreactive groups as pendant groups on the copolymer, for instance amine or, more usually, hydroxyl groups. Examples of reactive groups capable of crosslinking with such pendant groups or of reacting to provide covalent binding to a surface, an aldehyde group or a silane or siloxane group containing one or more reactive substituents such as halogen, for example chlorine, or alkoxy, generally containing from 1 to 4 carbon atoms, for example methoxy or ethoxy, or, more preferably, Q3 is a hydroxyl, amino, carboxyl, epoxy, —CHOHCH$_2$Hal, (in which Hal is a halogen atom such as chlorine, bromine or iodine) succinimido, tosylate, triflate, imidazole carbonyl-amino or optionally substituted triazine group. A preferred example of a reactive group is a trimethoxysilyl group which reacts either with other similar groups or with hydroxyl groups on the terpolymer or a substrate.

Preferred reactive comonomers IV which are used to crosslink the comonomer, rather than provide covalent binding to the surface, are those $Q^3$ contains a crosslinkable cinnamyl, epoxy, —CHOHCH$_2$Hal (in which Hal is a halogen atom), methylol, reactive silyl, an ethylenically unsaturated crosslinkable group, such as an acetylenic, diacetylenic, vinylic or divinylic group, or an acetoacetoxy or chloroalkyl sulfone, preferably chloroethyl sulphone, group. For optimum cross-linking a monomer including a reactive silyl group is used in combination with a further monomer including a hydroxyl group.

Such polymers may include a diluent monomer, for instance of the types described below.

It is believed that quater polymers of a zwitterionic monomer of formula I above, a cationic monomer of formula II above, a reactive monomer of formula IV in which $Q^3$ is a trialkoxysilyl group and a quater monomer of the formula IV in which $Q^3$ is a hydroxyl group are new and are claimed herein.

In each of the monomers I to IV the ethylenically unsaturated group is preferably selected from

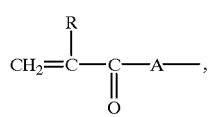 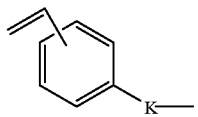

CH$_2$=C(R)—CH$_2$—O—, CH$_2$=C(R) —CH$_2$OC(O)—, CH=C(R)OC(O)—, CH$_2$=C(R)O—, and CH$_2$=C(R) CH$_2$OC(O)N(R$^1$)— wherein:

R is hydrogen or a $C_1$–$C_4$ alkyl group;

A is —O— or —NR$^1$— where R$^1$ is hydrogen or a $C_1$–$C_4$ alkyl group or R$^1$ is —B—X, B$^1$Q$^1$, B$^2$Q$^2$ or B$^3$Q$^3$ where B, B$^1$, B$^2$, B$^3$, Q$^1$, Q$^2$ and Q$^3$ and X are as defined above in the respective formula I to IV and K is a group —(CH$_2$)$_p$OC(O)—, —(CH$_2$)$_p$C(O)O—, —(CH$_2$)$_p$OC(O)O—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O)NR$^2$—, —(CH$_2$)$_p$NR$^2$C(O) NR$^2$—, (in which the groups R$^2$ are the same or different) —(CH$_2$)$_p$O—, —(CH$_2$)$_p$SO$_3$—, or, optionally in combination with B, a valence bond and p is from 1 to 12 and R$^2$ is hydrogen or a $C_1$–$C_4$ alkyl group.

Preferably the ethylenically unsaturated groups of all monomers copolymerised together are either the acrylate type or are the styrene type, and, most preferably each has the same formula. Preferably the groups A of acrylate type ethylenically unsaturated groups of the zwitterionic, cationic and termonomer are the same and are most preferably all —O—.

The zwitterionic group X preferably has a phosphate ester group as the anion or the thioester analogue or amide analogue or a phosphonate. The cationic moiety is preferably a quaternary ammonium group, but may be a sulphonium or phosphonium group. Preferably the cationic group is at the end of the group X distant from the group B.

Preferably X is a group of formula

(VI)

in which the moieties X$^1$ and X$^2$, which are the same or different, are —O—, —S—, —NH— or a valence bond, preferably —O—, and W$^+$ is a group comprising an ammonium, phosphonium or sulphonium cationic group and a group linking the anionic and cationic moieties which is preferably a $C_{1-12}$-alkylene group.

Preferably W contains as cationic group an ammonium group, more preferably a quaternary ammonium group.

The group W$^+$ may for example be a group of formula —W—N$^+$R$^{23}$$_3$, —W$^1$—P$^+$R$^{23a}$$_3$, —W$^1$—S$^+$R$^{23a}$$_2$ or —W$^1$—Het$^+$ in which:

W$^1$ is alkylene of 1 or more, preferably 2–6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group W$^1$ optionally contains one or more fluorine substituents and/or one or more functional groups; and either the groups R$^{23}$ are the same or different and each is hydrogen or alkyl of 1 to 4 carbon atoms, preferably methyl, or aryl, such as phenyl or two of the groups R$^{23}$ together with the nitrogen atom to which they are attached form a heterocyclic ring containing from 5 to 7 atoms or the three groups R$^{23}$ together with the nitrogen atom to which they are attached form a fused ring structure containing from 5 to 7 atoms in each ring, and optionally one or more of the groups R$^{23}$ is substituted by a hydrophilic functional group, and the groups $R^{23a}$ are the same or different and each is $R^{23}$ or a group $OR^{23}$, where $R^{23}$ is as defined above; or Het is an aromatic nitrogen-, phosphorus- or sulphur-, preferably nitrogen-, containing ring, for example pyridine.

Preferably $W^1$ is a straight-chain alkylene group, most preferably 1,2-ethylene.

Preferred groups X of the formula VI are groups of formula VA.

The groups of formula (VA) are:

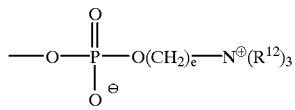

(VA)

where the groups $R^{12}$ are the same or different and each is hydrogen or $C_{1-4}$ alkyl, and e is from 1 to 4.

Preferably the groups $R^{12}$ are the same. It is also preferable that at least one of the groups $R^2$ is methyl, and more preferable that the groups $R^{12}$ are all methyl.

Preferably e is 2 or 3, more preferably 2. When X is a group of formula (VA) preferably B is a group of formula —$(CR^{13}{}_2)$— or —$(CR^{13}{}_2)_2$—, eg. —$(CH_2)$— or —$(CH,CH_2)$—.

Preferably the zwitterionic monomer has the general formula VI

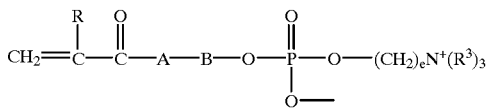

VI wherein

R, A and B are defined above, the groups $R^3$ are the same or different and each is hydrogen $C_{1-1}$ alkyl, aryl, alkaryl, aralkyl, or two or three of the groups $R^1$ with the nitrogen atom to which they are attached form a saturated or unsaturated hetero cyclic ring, and e is 1 to 6, preferably 2 to 4.

A cationisable moiety in the group $Q^1$ is generally a group which can easily be protonated to render it cationic, for instance which is protonated in aqueous environments at pH7.

The group $Q^1$ of the cationic monomer is preferably a group $N^+R^5{}_3$, $P^+R^5{}_3$ or $S^+R^5{}_2$ in which the groups $R^5$ are the same or different and are each hydrogen, $C_{1-4}$-alkyl or aryl (preferably phenyl) or two of the groups $R^5$ together with the heteroatom to which they are attached from a saturated or unsaturated heterocyclic ring containing from 5 to 7 atoms. Preferably the group $Q^1$ is permanently cationic, that is each $R^5$ is other than hydrogen. Preferably $Q^1$ is $N^+R^5{}_3$ in which each $R^5$ is $C_{1-4}$-alkyl, preferably methyl.

Monomer formulations suitable for forming the novel terpolymers and novel quater polymers are claimed herein. Liquid compositions containing the terpolymers and quater polymers and a solvent are claimed herein as are processes in which the liquid composition is coated onto a surface and the solvent is removed to leave a coating on the surface.

By incorporating pendant groups to provide stable binding on the surface, the terpolymers and quater polymers can be stably bound to many types of underlying surface, for subsequent provision of a coated substrate for receiving heparin.

In a new application of the novel terpolymer or quater polymer according to the invention a substrate having a coating of the polymer is contacted with a solution having suspended or dissolved therein an anionically charged mucopolysaccharide.

The anionically charged mucopolysaccharide may be heparin or a similar anti-thrombogenic compound such as hirudin or chondroitin sulphate, or may be alginate or hyaluronic acid. The provision of cationic pendant groups at the substrate surface on the coating provides a charged entity, having the opposite charge to that of the mucopolysaccharide, enabling the mucopolysaccharide to become counterionically bonded to the surface in the contacting step. The zwitterionic groups seem to minimise adsorption of other components from blood or biological fluids subsequently contacted with the coated surface, thereby preventing fouling of the surface which would mask the mucopolysaccharide's effect.

The mucopolysaccharide coating may be carried out as the second step of a two step process. In the first step a substrate is coated with a liquid composition containing the polymer suspended or dissolved in a solvent, followed by removal of the solvent prior to the mucopolysaccharide coating step.

Alternatively the pendant groups $Q^3$ and/or $Q^4$ may provide compatibility with other polymers when blended, for instance by solid or liquid blending techniques. Thus pendant hydrophobic groups may interact with hydrophobic blended copolymers whilst reactive groups may be crosslinked, for instance during reactive blending processes or after blending has taken place. Such blends can subsequently be used to form shaped articles which may be coated with heparin in a post shaping step. The novel polymers themselves may have satisfactory properties such that they may be useful to form components of devices which can be treated with heparin to improve their anti-thrombogenicity.

The novel terpolymer may be blended with heparin in a pre-blending step and the complex subsequently used to form coatings or be used in a blend with other polymers having desirable mechanical characteristics. A blend may, for instance, be made by dispersing both components in a solvent in which they are both compatible. Alternatively each component is dissolved or dispersed in a solvent which is suitable for the respective component and the two liquid compositions mixed. Other components may be included to stabilise the mixture. Such pre-blended heparin/polymer complexes are primarily of use as coating components, that is for forming deposits from liquid coating compositions onto underlying substrate surfaces.

A complex formed by crosslinking anionic mucopolysaccharides by the novel terpolymer forms a further aspect of the present invention. The cationic groups of the polymer provide intermolecular ionic crosslinking with the mucopolysaccharide molecules.

The zwitterionic terpolymer or quater polymer and the anionic mucopolysaccharide are generally used in ratios of equivalent ionic groups in the range 1:10 to 10:1, preferably about 1:2 to 2:1, probably about 1:1. The use of such ratios allows the formation of a crosslinked mucopolysaccharide which may have suitable characteristics such that a gel, comprising a liquid component in which the crosslinked mucopolysaccharide is swellable but not soluble. Such gels may be used for instance as wound dressings, microbial culture media, drug delivery systems, etc. The dry crosslinked materials may be used as absorbent materials for absorbing aqueous or organic solvent based liquids.

The novel terpolymers or quaterpolymers may also be used in ion exchange resins or in other separation processes.

For instance particles or membranes of or coated by the terpolymer or quater polymer may be used to remove anionic components from liquids in which they are suspended or dissolved. This use of the zwitterionic/cationic resins minimises adsorption from such a liquid of other components, by reducing the extent to which such other components adhere to the resin through the activity of the zwitterionic groups. This minimises fouling of the resin by components other than those intended to be ion exchanged. This may also be desirable where the resin is used to remove anionic components from fluids intended to be subsequently introduced or reintroduced into a patient's body. In this aspect, blood may be circulated through a bed of particles of such a resin or through a membrane or other filter formed of such a resin to remove heparin from the circulation in a patient subjected to heparin treatment for surgery or other reasons.

We have found that the terpolymers and quater polymers described in the examples herein can be used successfully to coat various substrates including polyesters, polycarbonates polypropylene, polyvinyl chloride and steel and filters may include coated surfaces of any of these materials.

Instead of passing anticoagulant-treated blood through an extra corporeal filter, heparin (or other anticoagulant) scavenging may be carried out by implanting, permanently or temporarily, a device into the body in the circulation, which can remove anticoagulant which has been administered systemically. Thus the terpolymer or quater polymer may be coated onto the surface of a vascular stent introduced into a blood vessel of a patient. In this embodiment the device may act as a reservoir, formed in situ, of active ingredient which may be released slowly into the circulation over an extended period of time. Alternatively a device may be preloaded with counterionically charged mucopolysaccharide prior to implantation, to act as a slow release drug delivery system.

The proportions of zwitterionic and cationic pendant groups in the novel polymers depends upon the desired end use. Where high levels of mucopolysaccharide are to be scavenged from a fluid composition and/or it is desired for a high density of anionic mucopolysaccharide to be deposited onto a surface for subsequent use, then the amount of cationic pendant group should be relatively high as compared to the levels of zwitterionic groups. However where lower levels of mucopolysaccharide are required to be adsorbed to achieve anti-thrombogenic performance, whilst minimising deposition of protein and lipid components and platelets forms an important characteristic of the surfaces, then high levels of zwitterionic pendant groups are likely to be desirable. The relative ratios (equivalents) is in the range 1:100 to 100:1 (zwitterionic to ionic) preferably 1:10 to 10:1, more preferably 1:2 to 20:1.

The total molar proportion of monomer of the formula III or IV in the polymer may be in the range 0.1 to 75%.

The polymers may include diluent comonomer. Such diluent comonomer may be used in quantities up to 90 mol %, usually less than 50 mol %. Copolymerisable nonionic monomers may be used such as $C_{1-24}$ alkyl(meth)acrylates, -(meth)acrylamides, and hydroxy $C_{1-24}$alkyl(meth)acrylates and (meth)acrylamides.

The terpolymers may include anionic pendant groups, to provide intermolecular crosslinking by counterionic bonding with cationic groups. In such cases, the equivalent level of anionic groups is lower than that of cationic groups in order that the polymer has an overall cationic charge. Anionic copolymerisable monomers may be used, for instance in which the anionic group is derived from carboxylic, sulphonic or phosphonic acid.

It has been found that the binding of heparin and the terpolymer or quaterpolymer to a surface provides a coated substrate in which the heparin appears to be in a condition such that good anti-thrombogenic properties are exhibited. Furthermore the coating is very stable and resistant to fouling during use such that the heparin conferred properties are retained even after substantial periods of use. Thus the performance is found to be greatly improved as compared to normal heparin treated surfaces. The binding of heparin to pretreated surfaces which have pendant cationic and zwitterionic groups is achieved merely by contacting the surface with heparin in solution, whereby heparin becomes bound to the cationic groups via counterionic bonding.

The following examples illustrates the inventions.

Performance Tests

Heparin Activity

Loading of samples with heparin

1. Filter strips.

Samples were incubated with 5 ml of a solution of heparin in PBS (usually 50 U/ml. In other experiments, a heparin concentration of 4 or 200 U/ml in saline produced the same heparin surface activity on the cationic polymer) for 30 min on a test tube shaker at room temperature. After 30 min, the samples were rinsed for 10 sec on both sides first with PBS then with deionized water. The samples were dried on tissue paper and in air and stored at room temperature.

2. Whole filters.

Arterial filters were filled with 100 ml of a heparin solution in PBS (50 U/ml) and inlet/outlet sides were closed. The filter was rotated for 30 min, ensuring that all parts of the device were in contact with the heparin loading solution. The filter was then drained and filled/drained 3 times with PBS and then filled/drained 3 times with deionized water. The filter was dried by a stream of air and stored at room temperature.

Preparation of Samples for Heparin Test

Heparin loaded filter strips (dip-coated or removed from whole arterial filters) were usually incubated for 5 hrs at 37° C. in PBS/BSA 1%/NaN$_3$ 0.1% to remove unstable bound heparin. The samples were then rinsed with PBS and deionized water as described and dried in air. Samples of 0.2–0.4× 0.4 cm were cut out and tested as described below.

Heparin Test

A chromogenic assay (Heparin CRS106, Sigma). The "Semi-Micro Method" described in the manual was used. Heparin loaded coated samples were placed in polystyrene test tubes. The tubes were placed into a 37° C. water bath (5 tubes). 200 μl of bovine factor Xa was added and the tubes were shaken. Following 1 min agitation, 200 μl factor Xa substrate was added to the tubes and they were agitated for 5 min. 200 μl acetic acid (>90%) was added to the tubes and the tubes were shaken. 200 μl of the solution was removed from the tubes and added to the well of a microplate (2 wells/sample) and measured at 405 nm against wells containing 200 μl of PBS. Previous results had shown that PBS gave the same absorbance reading as a reagent blank. The heparin activity was calculated with the use of a standard curve prepared with soluble heparin.

Platelet Adhesion

Heparin loaded and heparin free samples were incubated with human blood (citrate or heparin as anticoagulant) for 2–3 hrs and the degree of platelet adhesion was determined by scanning electron microscopy.

Fibrinogen Absorbance

Samples of heparin loaded or heparin-free coated material were incubated with human plasma for 10 min, washed with PBS/BSA 1%, then incubated for 30 min with an anti-human fibrinogen antibody conjugated to horse radish peroxidase (Dako Code No. A080). The samples were washed and bound antibody was determined by incubating the samples with a substrate for peroxidase (0-phenylenediamine dihydrochloride, 0.4 mg/ml) and a phosphate citrate buffer with urea hydrogen peroxide (Sigma P-9305). After 10 min the absorbance at 450 nm was measured against a reagent blank.

Perfusion with Bovine Blood

Two arterial filters (a control filter and a coated heparin loaded filter or a coated non-heparin loaded filter) were perfused in parallel for 6 hrs with bovine blood (3.5 L/min) at reduced heparin concentrations and macroscopic blood clots were detected visually and photographs were taken.

Observed Chloride

The counter ion in the polymeric system is chloride ion. Quantification of the chloride ion allows the level of cationic methacrylate to be determined.

Procedure

Add 0.25 g polymer to 25 ml methanol. Once the material has fully dissolved add 75 ml of distilled water to the polymer/methanol mixture. Adjust the pH of the mixture to fall between 8–9. Add 1.0 ml of potassium chromate (5% in w/v distilled water) by pipette to the flask, and titrated to the first brown/red end-point with standardised 0.01 m silver nitrate solution. Repeat the titration, using 75 ml distilled water, but no polymer sample to obtain a blank reading. The level of cationic methacrylate in the polymer is directly proportional to the chloride ion concentration.

EXAMPLE 1

Preparation of poly (2(methacryloyloxyethyl)-2' trimethylammonium) ethyl phosphate innersalt-co-n-dodecyl methacrylate-co-11 methacryloylundecyl-1-trimethyl ammonium bromide) (40:71:8).

2- (Methacryloyloxyethyl) -2'-(trimethyl ammonium) ethyl phosphate inner salt (2.32 g, 0.0079 mole), n-dodecyl methacrylate (3.61 g, 0.0142 mole) and 11 methacryloylundecyl-l-trimethyl ammonium bromide (0.59 g, 0.0016 mole synthesised according to reference example 1) were dissolved in 43 ml of propan-2-ol and 17 ml of ethyl acetate.

This monomer solution was thoroughly degassed by bubbling dry nitrogen gas (dried over molecular sieve) through it for 30 minutes. The initiator, AIBN (0.01360 g, 0.02 weight % of solution) was then washed into the solution using 3 ml of degassed ethanol. The solution was further degassed for five minutes. Maintaining the solution under a slight positive pressure of nitrogen (equivalent to a few ml of mineral oil in a bubbler) the solution was heated to 62° C. and stirred vigorously for around 46 hours.

After this time the reaction mixture was allowed to cool to around 40° C. before removing all of the solvent using a rotary evaporator under vacuum and at about 40° C. giving a solid foam.

This foam was then dissolved in 24 ml of dichloromethane and precipitated dropwise into an excess, 200 ml, of acetone. The product was collected on a Buchner filter funnel and washed with 3 further 20 ml quantities of acetone. The white solid was dried in a vacuum oven for 16 hours at 40° C. and weighed.

The resulting polymer, obtained in 83% yield, was a white solid.

$^1$HNMR (400 MHz, d, ppm, $CD_3OD/CDCl_3$) 4.31(b), 4.21(b), 4.07(b), 3.98(b), 3.72(b),3.37, 3.33, 3.29(s), 3.22, 3.17, 1.95, 1.84(b), 1.67(b), 1.33(s), 1.06(b), 0.93(s), $C_{10}$ NMR (500 MHz, d, ppm, $CD_3OD/CDCl_3$) 176.37, 66.91, 65.90, 63.68, 60.05, 54.50, 53.37, 45.54, 32.69, 30.44, 30.13, 28.92, 26.93, 23.41, 17.31, 14.56.

EXAMPLE 2

Preparation of poly (2(methacryloyloxyethyl)-2' trimethylammonium) ethyl phosphate innersalt-co-n-dodecyl methacrylate-co-cholinemethacrylate Using a similar technique to that used in Example 1, but using choline methacrylate (2-methacryloyloxy-ethyl trimethyl ammonium chloride) in place of 11-methacryloyl undecyl-1-trimethyl ammonium bromide, various polymerisations were carried out. The zwitterionic monomer, lauryl (dodecyl) methacrylate monomer and choline methacrylate were mixed at the molar ratio shown in Table 1 below and AIBN as initiator was used at the level shown in the table. The total weight percent of solids in the polymerisation solution is also reported in the table, since it was varied between examples.

The polymers were recovered by essentially the same method as in claim 1 although including an extra dissolution and precipitation step to remove lower molecular weight polymer.

The polymer product was subjected to chloride ion determination to establish the rate of inclusion of cationic monomer into the product. Also some rough molecular weight determinations were carried out.

EXAMPLE 3

Preparation of Poly(2-(Methacryloyloxyethyl)-2'-(Trimethylammoniumethyl) Phosphate, Inner Salt)-co-(n-Dodecyl methacrylate)-co-(2-(Methacryloyloxy) ethyl trimethyl ammonium chloride)-co-(3-Trimethyoxysilylpropyl methacrylate) 30:60:6:4 terpolymers 3.1 Monomer Feed Synthesis The zwitterionic monomer (40.68 g, 0.138 mole) and cationic monomer (5.73 g,0.0275 mole) were weighed in a glove box environment dried by $P_2O_5$ Dodecyl methacrylate (69.45 g, 0.273 mole), trimethoxysilyl monomer (4.53 g,0.0182mole) and a-azo-isobutyronitrile (AIBN) initiator (1.202 g, 1%) were weighed in air. A 3 neck reaction flask, fitted with water condenser, nitrogen gas flow and monomer feed tubing, and primed with anhydrous n-propanol (60 g) solvent, was immersed in a heated 90° C. oil bath. The monomers and initiator were dissolved in 300 g of n-propanol solvent and magnetically stirred in a measuring cylinder sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2.25 hours. The reaction was stirred for another hour. A second charge of AIBN initiator (0.12 g), dissolved in 3 ml n-propanol, was added and the reaction mixture was stirred for a further 50 min, taking the total reaction time to 4 hours.

Once cooled to room temperature, the reaction mixture was filtered through a sintered glass filter. The solvent was removed at 40° C.–50° C. by rotary evaporator to give a white foam residue that was later redissolved in 480 ml dichloromethane and 40 ml methanol solvent mixture and dropwise precipitated into 4000 ml acetone. A white solid product settled from the acetone leaving a slightly cloudy supernatant. The product was separated by Buchner flask and 113 Whatman wet strenghtened filter paper, and dried in a room temperature vacuum oven for up to 24 hours prior to a second workup and precipitation in acetone. The product was weighed (82.9 g) to provide a 68.9 wt % yield, bottled in a brown glass vial and refridgerated.

Characterisation of Product

The polymer requires by weight C 63.08%, H 10.13%, P 3.55%, N 1.93%, Si 0.43% Cl 0.81%, found C 58.1%, H 9.98%, P 3.09%, N 1.90%, Si 0.20%, $^1$Hnmr (400 MHz, ppm, $CD_3OD:CDCl_3$ 1:1 v:v) 4.34, 4.30, 3.98, 3.72, 3.38, 3.29, 3.22, 1.67, 1.32, 0.92, 0.10. Specific viscosity of 10 mg/ml solution in ethanol:chloroform (1:1 v:v) is 0.13. The polymer product was subjected to the chloride ion assay to establish the rate of inclusion of cationic monomer; required 4.76 wt %, found 4.82 wt % and 4.94 wt %.

3.2 One Pot Synthesis

Zwitterionic monomer (4.87 g, $1.65 \times 10^{-2}$ mole), dodecyl methacrylate (8.11 g, $3.19 \times 10^{-2}$ mole), cationic monomer (0.67 g, $0.32 \times 10^{-2}$ mole) and trimethoxy-silyl monomer (0.53 g, $0.21 \times 10^{-2}$ mole) were rinsed into the reaction vessel with 114 ml solvent mixture of 15:85 v/v % MeOH:EtOH. Anhydrous cationic monomer was predissolved in 3 ml pure MeOH before being rinsed into the reaction vessel. Dodecyl methacrylate monomer was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g) being rinsed into the reaction mixture with 2 ml solvent mixture. The reaction was magnetically stirred and maintained up a positive pressure nitrogen blanket sufficient to bubble through a mineral oil bubbler. The reaction time was 39 hours.

Once cooled to room temperature, the reaction mixture appeared clear with a slight haze. The solvent was removed at room temperature by rotary evaporator to give a white foam residue that was later redissolved in 50 ml dichloromethane and added dropwise into vigorously stirred 500 ml acetone. A white solid product settled from the acetone leaving a slightly cloudy supernatant. The product was separated by Buchner flask and 113 Whatman wet strengthened filter paper, and dried in a room temperature vacuum oven for up to 72 hours. The product was weighed to provide a 91 wt % yield, bottled in a glass jar and refrigerated.

Characterisation

The polymer requires by weight C 62.93%, H 10.11%, P 3.61%, N 1.95%, Si 0.42% Cl 0.80%, found C 57.88%, H 10.20%, P 3.30%, N 1.84%, Si 0.12% Cl 0.78%; $^1$Hnmr (400 MHz, ppm, $CD_3OD:CDCl_3$ 1:1 v:v) 4.33, 4.29, 3.97, 3.71, 3.38, 3.34, 3.29, 3.22, 1.67, 1.32, 0.92, 0.09; specific viscosity in a 10 mg/ml solution of ethanol:chloroform (1:1) is 0.32.

EXAMPLE 4

Preparation of Poly(2-Methacryloyloxyethyl)-2'-(Trimethylammoniumethyl) Phosphate, Inner Salt)-co-n-Dodecyl methacrylate)-co-(2-Methacryloyoxy) ethyl trimethyl ammonium chloride)-co-(hydroxy propyl methacrylate)-co-(3-Trimethoxysilylpropyl methacrylate) 23:47:6:20:4 polymers.

4.1 Monomer Feed Synthesis

Zwitterionic monomer (34.10 g, 0.116 mole) and cationic monomer (6.3 g, 0.030 mole) were weighed in a glove box environment dried by $P_2O_5$. Dodecyl methacrylate (60.01 g, 0.236 mole), hydroxypropyl methacrylate monomer (14.51 g, 0.101 mole), trimethoxysilyl monomer (5.00 g, 0.020 mole) and AIBN initiator (0.2409 g, 0.2%) were weighed in air. A 3 neck reaction flask, fitted with water condenser, nitrogen gas flow and monomer feed tubing, and primed with anhydrous n-propanol:isopropyl acetate (60:40 mass ratio) solvent, was immersed in a heated 90° C. oil bath. The monomers and initiator were dissolved in n-propanol:isopropyl acetate solvent and magnetically stirred in a measuring cylinder sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2 hours. The reaction was stirred for another hour. A second charge of AIBN initiator (0.0241 g, 0.02 wt %) was added and the reaction mixture was stirred for a further hour, taking the total reaction time to 4 hours. Total solids content was 30 wt % in n-propanol:isopropyl acetate (168.06 g:112.08 g).

Once cooled to room temperature, the reaction mixture was split into two batches. The first batch of reaction mixture (240 ml) was precipitated by dropwise addition to vigorously stirred methyl acetate (2000 ml). The product was separated by Buchner flask and 113 Whatman wet strengthened filter paper, and dried in a room temperature vacuum oven for up to 24 hours. The product was rapidly frozen by liquid nitrogen, milled into a fine powder and further dried in a room temperature vacuum for 24 hours. The product (50.67 g, 81.8% based on mass recovery) was bottled in a brown glass vial and stored at 4° C.

The polymer requires by weight C 62.4%, H 9.9%, P 3.0%, N 1.9%, Si 0.4% Cl 0.8%, found C 57.0%, H 9.4%, N 1.7%, P 2.7%; $^1$Hnmr (400 MHz, ppm, $CD_3OD:CDCl_3$ 1:1 v:v) 4.41, 4.08, 3.83, 3.46, 3.40, 3.34, 2.07, 1.67, 1.43, 1.18, 1.04.

The product was subjected to chloride ion assay to establish the rate of inclusion of cationic monomer: required 5.23 wt %, found 4.66 and 4.71 wt %.

4.2 One Pot Synthesis

Zwitterionic monomer (3.98 g, $1.35 \times 10^{-2}$ mole), dodecyl methacrylate monomer (7.009 g, $2.76 \times 10^{-2}$ mole), cationic monomer (0.733 g, $0.35 \times 10^{-2}$ mole), hydroxypropyl methacrylate (1.691 g, $0.67 \times 10^{-2}$ mole) and trimethoxysilyl monomer (0.585 g, $0.24 \times 10^{-2}$ mole) were rinsed into the reaction vessel with 98 ml solvent mixture of 15:85 v:v % MeOH:EtOH. Anhydrous cationic monomer was predissolved in 3 ml pure MeOH before being rinsed into the reaction vessel. Dodecyl methacrylate was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g, 1.1 wt %) being rinsed into the reaction mixture with 2 ml solvent mixture. The reaction was magnetically stirred and maintained under a positive pressure nitrogen blanket sufficient to bubble through a mineral oil bubbler. The reaction time was 39.5 hours.

Once cooled to room temperature, the reaction mixture was filtered through sintered glass. The solvent was removed at <40° C. by rotary evaporator to give a white foam residue that was later redissolved in 58 ml dichloromethane and added dropwise into vigorously stirred 600 ml acetone. A white solid product settled from the acetone leaving a slightly cloudy supernatant. The product was separated by Buchner flask and 113 Whatman wet strengthened filter paper, and dried in a room temperature vacuum oven for up to 20 hours. The product was milled, further dried in a room temperature vacuum for 24 hours and weighed to provide a 93.2 wt % yield, bottled in a glass jar and refrigerated.

The polymer requires by weight C 62.41%, H 9.91%, P 2.99%, N 1.70%, Si 0.47% Cl 0.89%, found C 58.45%, H 9.45%, P 2.55%, N 1.65% Si 0.34%, Cl 1.06%. $^1$Hnmr (400 MHz, ppm, $CD_3OD:CDl_3$ 1:1 v:v) 4.33, 4.29, 3.97, 3.71, 3.38, 3.34, 3.29, 3.22, 1.67, 1.32, 0.92, 0.09. Specific viscosity of 10 mg/ml solution in ethanol is 0.33. The polymer product was subjected to the chloride ion assay to establish the rate of inclusion of cationic monomer; required 5.24 wt %, found 5.16 wt % and 5.26 wt %.

EXAMPLE 5

Preparation of Poly(2Methacryloyloxyethyl) 2' (Trimethylammoniumethyl) Phosphate, Inner Salt)-co-(n Dodecyl methacrylate)-co-(2Methacryloyloxy) ethyl trimethyl ammonium chloride) 33.3:60:6.7 terpolymers.

Monomer Feed Synthesis

To anhydrous n-propanol: isopropyl acetate (30.0 g: 8.0 g) solvent mixture at room temperature, zwitterionic monomer (13.5 g, $4.58 \times 10^{-2}$ mole) dodecyl methacrylate (20.9 g, $8.23 \times 10^{-2}$ mole) cationic monomer (2.5 g, $1.20 \times 10^{-2}$ mole) were added. To the mixture, AIBN (0.7 g, 0.20 wt %), dissolved 4 g isopropyl acetate, was added. The stirred mixture was parafilm sealed in a measuring cylinder and dropwise added via a peristaltic pump to stirred anhydrous n-propanol: isopropyl acetate (27 g:20 g) solvent mixture immersed in a heated 90° C. oil bath under $N_2$ gas flow. Complete transfer took 2 hours. The pump tubing was washed with isopropyl acetate (4 g) and n-propanol 4 g) into the 90° C. reaction mixture. The reaction was stirred for another hour, where upon AIBN, (0.01 g, 0.02 wt %) dissolved 2 ml isopropyl acetate, was added, the pump tubing was washed with isopropyl acetate (2 g) and the reaction was stirred for a further hour.

The heating was stopped after 4 hours and the reaction mixture was pumped to ethyl acetate (450 g) at room temperature followed by a pump line wash of n-propanol (3 g). The product was allowed to settle and the supernatant was decanted. Product was dissolved with isopropanol (47 g) solvent, pumped to ethyl acetate (720 g) for 45 minutes, the pump line washed with isopropanol (6 g) and the product allowed to settle. The supernatant was decanted and the product was washed with acetone (160 g) by stirring for 10 minutes. The supernatant was decanted and the product was filtered (Whatman 13 wet strengthened paper) with an acetone wash (80 g). The product was dried at room temperature in a vacuum deccicator for up to 16 h, weighed (31.6 g, 87% yield based on mass recovery) and stored in a brown glass vial at 4° C.

Characterisation $^1$Hnmr (400 MHz, ppm, $CD_3OD:CDCl_3$ 1:1 v:v) 4.41, 4.08, 3.83, 3.46, 3.40, 3.34, 2.07, 1.67, 1.43, 1.18; Specific viscosity of 10 mg/ml solution in ethanol is 0.26.

The polymer was subjected to chloride ion assay to establish the inclusion of cationic monomer, required 5.23 wt %, found 5.28 and 5.36 wt %.

EXAMPLE 6

Samples of some of the polymers of examples 1 and 2 were tested for their performance in terms of fibrinogen adsorption and heparin activity. A coating solution of the polymer 10 mg/ml in isopropyl alcohol, was made up and used to coat the surface of samples of polyethylene terephthalate (p.e.t.). The p.e.t. sample to be subjected to a fibrinogen assay was a 1×3 cm sheet, whilst that to be subjected to a heparin assay was 40 micron arterial filter material. The dried coating was subsequently contacted with heparin solution 50 U/ml in PBS, rinsed first with PBS and then with deionised water and dried. The polymer/heparin coated substrate was subjected to the fibrinogen and heparin tests mentioned above. The results for the heparin activity and fibrinogen adsorption for the polymers of example 2 are given in Table 2 below.

Furthermore example 1 polymer/heparin coated materials were subjected to a stability test. For this the polymer (example 1)/heparin coated substrates were immersed in 1% serum albumin in phosphate buffered saline for periods in the range 0.5 to 6 hours at 37° C. The treated samples were removed, rinsed first with PBS and then with deionised water, and the heparin activity measured. The results indicate that there is no significant loss of activity after 6 hours of BSA/PBS incubation, whereas comparative tests carried out on the commercially available Duraflo and Medtronic M-40 surfaces showed very poor stability. The results using the Carmeda Bioactive surface showed equivalent stability.

EXAMPLE 7

As a further performance test, substrates coated with example 1 polymer, with and without heparin loading, were contacted with heparinised blood 15 U/ml for 60 minutes. The treated samples were removed, rinsed first with PBS and then with deionised water and the heparin activity measured. The results show that surfaces coated with the polymer with pendant cationic and phosphoryl choline groups attract and bind heparin from blood which contains heparin. The surfaces were also studied under s.e.m. and no biological deposits (e.g. of platelets, blood cells and protein) were observed, for the heparin loaded sample or the non-heparin loaded sample.

As comparisons, tests were also carried out on three commercially available heparinised surfaces. DuraFlo uses ionically bound heparin; Medtronic M-40 is believed to use ionically bound heparin; Medtronic CBM-40 (Carmeda Bioactive) uses end point attached heparin.

For these experiments, filter samples were incubated at room temperature with 5 ml of phosphate buffered saline (PBS) with or without 1% serum albumin (BSA) or fresh heparinized human blood. After 60 min, the samples were rinsed thoroughly with saline and deionised water and heparin activity was measured.

The results are shown in Table 3.

Before incubation with PBS, the heparin activity on the DurafloII sample was 240 mU/cm$^2$ and 33.5 mU/cm$^2$ on the Medtronic M40. The Carmeda BioActive Surface heparin appeared to be more stable with BSA, but the initial heparin activity was the lowest of all filters tested. Previous results have shown that another 20 micron Medtronic filter with Carmeda bonded heparin had only 2,3 mU/cm$^2$.

Table 3 shows that the polymer of the invention attracts and binds heparin from the blood sample which had a heparin concentration of 15 U/ml.

Initial results had shown that the coating not loaded with heparin shows heparin activity following incubation with heparin containing human blood (see Table 3).

Two similar arterial filters were coated with the cationic/zwitterionic heparin binding polymer of example 1. Only one filter was loaded with heparin as described above, the other filter was only washed with PBS. Both filters were perfused in parallel with bovine blood (3.5 L/min) for 6 hrs. The blood contained 644 U heparin/kg. The activated clotting time (measured by the Hemochron method) of the system was 447 sec after 9 min perfusion and fell to 257 sec after 60 min perfusion. After 306 min perfusion, the activated clotting time was 212 sec. Both filters performed similar and showed significantly less blood clots than uncoated filters in similar previous perfusion experiments.

EXAMPLE 8

The polymer of example 4 was used to coat arterial filter devices. The filter was air plasma treated for 30s prior to coating. In a separate step two dispersions were made up. The first contained 2500 U heparin (bovine lung) in PBS (2.5 ml) and water (47.5 ml). The second contained 250 mg polymer in 50 ml isopropylalcohol. The two liquid compositions were mixed together then poured into the plasma treated filter which was shaken vigorously for 15 minutes to ensure contact of all the surfaces of the device with the coating mixture. The mixture was then drained out and the coated device washed three times with water. The rinsed filter was dried and placed in an oven overnight at 50° C. to ensure the reactive groups of the polymer had crosslinked.

EXAMPLE 9

Further samples of polymers of examples 1 and 3 to 5 were coated onto arterial filters using the coating solutions described in example 6. The filters were dip coated with the polymer solutions, which were then dried overnight. The polymers of examples 3 and 4 were kept at 70° C. overnight to ensure complete crosslinking. The filters were then tested for their fibrinogen adsorption using the performance test described above. Some samples of filter were, after coating with polymer, were loaded with heparin using the general test described above and then subjected to fibrinogen adsorption and heparin activity tests. The control was untreated filter. Table 4 shows the results for reduction in fibrinogen adsorption as compared to the control and heparin activity for the heparin loaded devices. Comparisons are quoted for two commercially available heparin coatings Medtronic CB-M40, believed to have covalently (end point attached) heparin and Medtronic M-40 believed to have ionically bound heparin, in terms of fibrinogen adsorption and heparin activity. The results show that heparin is adsorbed onto the polymer, the mechanism assumed to be an ion exchange process. The filters coated with the PC polymer have reduced fouling by fibrinogen.

TABLE 2

| Example | Heparin Activity mU/cm2 | Fibrinogen reduction % |
|---|---|---|
| 2.5 | 15.9 | 79 |
| 2.6 | 11.8 | 55 |
| 2.7 | 24.3 | 66 |
| 2.8 | 21.2 | 74 |
| 2.9 | 36.2 | 60 |
| 2.10 | 22.1 | 64 |
| 2.11 | 18.7 | 67 |
| 2.12 | 35.6 | 70 |
| 2.13 | 0.9 | 81 |
| 2.14 | 1.8 | 57 |
| 2.15 | 0 | 77 |

TABLE 3

| | Heparin activity in mU/cm2 following incubation with | | |
|---|---|---|---|
| Sample | PBS | PBS/BSA | BLOOD heparinised |
| DurafloII | 25.6 | 4.8 | 0 |
| Medtronic M-40 | 7.1 | 0.9 | 0 |
| Medtronic CBM-40 | 5 | 4 | — |
| Ex. 1/ Heparin | 33.1 | 18.1 | 16.4 |
| Ex 1 | — | 0 | 18.3 |

TABLE 4

| | Without Heparin | With Heparin Loading | |
|---|---|---|---|
| Polymer of Example | Loading % reduction fibrinogen | % reduction fibrinogen | Heparin activity MU/cm$^2$ |
| Control | 0 | 100 | |
| 1 | 92 | 87 | 42 |
| 3 | 90 | 82 | 14 |
| 4 | 91 | 88 | 13 |

TABLE 1

| Example | AIBN wt % | Total Solids % | Pm g | Pm Mol % | MI g | MI Mol % | Cm g | Cm Mol % | Temp C. | Yield % | Cl- Calc (mg/l) | Cl- Obs (mg/l) | MW |
|---|---|---|---|---|---|---|---|---|---|---|---|---|---|
| 2.1 | 2.0 | 14.7 | 5.4 | 36.6 | 8.4 | 57.0 | 0.9 | 6.4 | 61 | 75.6 | 83.6 | 76.6 | 900780 |
| 2.2 | 1.0 | 14.7 | 5.4 | 36.9 | 8.3 | 56.8 | 0.9 | 6.4 | 61 | 74.3 | 83.0 | 80.4 | 678664 |
| 2.3 | 0.2 | 14.7 | 5.4 | 36.6 | 8.4 | 56.9 | 1.0 | 6.5 | 61 | 70.5 | 84.7 | 74.7 | 1597718 |
| 2.4 | 0.1 | 14.7 | 5.4 | 36.7 | 8.3 | 56.8 | 1.0 | 6.5 | 61 | 70.7 | 84.8 | 81.4 | 1850975 |
| 2.5 | 0.2 | 12.2 | 5.5 | 37.4 | 8.7 | 59.2 | 0.5 | 3.4 | 61 | 57.7 | 44.4 | 68.0 | 616454 |
| 2.6 | 0.2 | 12.2 | 5.4 | 37.2 | 8.7 | 59.4 | 0.5 | 3.4 | 61 | 72.6 | 44.6 | 37.1 | |
| 2.7 | 0.2 | 12.3 | 5.4 | 37.0 | 8.3 | 56.8 | 0.9 | 6.2 | 61 | 48.3 | 81.0 | 84.0 | |
| 2.8 | 0.2 | 14.7 | 5.4 | 36.7 | 8.4 | 56.9 | 0.9 | 6.4 | 61 | 49.9 | 83.6 | 71.7 | 493906 |
| 2.9 | 0.2 | 14.7 | 5.4 | 36.7 | 8.4 | 56.9 | 0.9 | 6.4 | 61 | 67.3 | 83.6 | 73.4 | |
| 2.10 | 0.2 | 12.2 | 5.4 | 36.8 | 8.4 | 57.1 | 0.9 | 6.1 | 61 | 73.6 | 79.8 | 70.4 | 395537 |
| 2.11 | 0.2 | 13.4 | 5.4 | 36.6 | 8.4 | 57.0 | 0.9 | 6.4 | 61 | 77.8 | 83.4 | 74.3 | |
| 2.12 | 0.2 | 13.4 | 5.4 | 36.6 | 8.4 | 57.0 | 0.9 | 6.4 | 61 | 82.6 | 83.4 | 77.6 | 668891 |
| 2.13 | 0.2 | 12.4 | 5.5 | 37.0 | 6.9 | 46.3 | 2.5 | 16.7 | 61 | 75.4 | 224.4 | 226.0 | 346592 |
| 2.14 | 0.2 | 14.8 | 5.4 | 36.8 | 6.9 | 46.4 | 2.5 | 16.8 | 61 | 78.9 | 226.1 | 187.3 | |
| 2.15 | 0.2 | 12.5 | 5.5 | 36.3 | 4.6 | 30.4 | 5.0 | 33.3 | 61 | 68.7 | 467.9 | 524.0 | 685687 |

*The molecular weights are relative values of determinations by gel permeation chromatography (without calibration) but should approximate to Daltons TABLE 4-continued

| Polymer of Example | Without Heparin Loading % reduction fibrinogen | With Heparin Loading | |
|---|---|---|---|
| | | % reduction fibrinogen | Heparin activity MU/cm² |
| 5 | 91 | 89 | 39 |
| comparison covalently bound Heparin | N/A | 56 | 9 |
| comparison ionically bound Heparin | N/A | 7 | <1 |

Reference Example 1

Synthesis of 11-methacryloyl undecyl-1-trimethylammonium bromide.

Step 1

To a solution of 11-bromo-1-undecanol (5.05 g, 0.02 mol), triethylamine (2.86 g, 0.028 mol) in dry ethyl acetate (30 ml), a solution of methacryloyl chloride (3.03 g, 0.029 mol) in ethyl acetate (20 ml) was slowly added, and the resulting mixture stirred for 90 min at RT.

The solid was filtered off, and the solvents removed in vacuo to afford predominantly 1-bromo, 11-undecylmethacrylate (Yield 6.26 g, 97%). As no starting materials were observed by 1H NMR and TLC Rf 0.69 (chloroform/pet. ether 7:3, v/v), this material was carried through to the second step.

Step 2

The product of step 1 (6.26 g, 0.019 mol) was dissolved in dry acetonitrile (40 ml) and added to a mixture of trimethylamine (2.8 g, 0.047 mol) in acetonitrile (20 ml). The system was purged with nitrogen, and then sealed with a dry ice condenser. The reaction was heated to 50 degrees for 20 hr, and protected from light with aluminium foil.

The remaining trimethylamine was removed on a water pump, and then the solvents removed in vacuo to give an off-white powder. This was washed with ether (250 ml) and the white solid collected (5.67 g, 76% yield). The ether was evaporated to dryness, and the residue again treated with ether (100 ml) to yield further white solid (1.02 g, 13%). 1H NMR indicated that the desired product was formed.

What is claimed is:

1. A terpolymer having an overall cationic charge formed from ethylenically unsaturated monomers including a) a zwitterionic monomer of the formula I

YBX    I wherein

B is selected from the group consisting of a bond, and straight and branched alkylene, alkylene-oxa-alkylene, and alkyleneoligooxa-alkylene groups any of which optionally includes one or more fluorine substituents X is an organic group having a zwitterionic moiety; and Y is ethylenically unsaturated polymerisable group;

b) a cationic monomer of the formula II

Y¹B¹Q¹    II wherein

B¹ is selected from the group consisting of a bond, and straight and branched alkylene, alkylene-oxa-alkylene and alkylene-oligooxa-alkylene groups, any of which optionally includes one or more fluorine substituents;

Y¹ is an ethylenically unsaturated polymerisable group; and

Q is an organic group having a cationic moiety; and c) in a minimum amount of about 30 mole %, a termonomer of the formula III

Y²B²Q²    III wherein

Y² is an ethylenically unsaturated polymerisable group; and

B² and Q² together represent a $C_{6-24}$-alkyl group.

2. A terpolymer according to claim 1 in which Y, Y¹ and Y² are each independently selected from

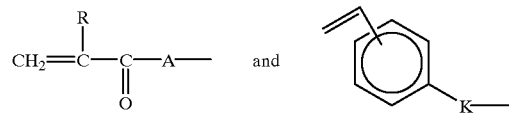

wherein:

R is hydrogen or a $C_1$–$C_4$ alkyl group;

A is —O— or —NR¹—where R¹ is hydrogen or a $C_1$–$C_4$ alkyl group or R¹ is —B—X, B¹Q¹ or B²Q² where B, Q¹, Q² and X are as defined above and K is selected from the group consisting of —$(CH_2)_pOC(O)$—, —$(CH_2)_pC(O)O$—, —$(CH_2)_pOC(O)O$—,—$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—,(in which the groups $R^2$ are the same or different) —$(CH_2)_pO$—, —$(CH_2)_pSO_3$—, and, optionally in combination with B, a valence bond and p is from 1 to 12 and $R^2$ is hydrogen or a $C_1$–$C_4$ alkyl group.

3. A terpolymer according to claim 1 in which B and B¹ each represent a straight or branched $C_{1-24}$ alkylene group.

4. A terpolymer according to in which X is an ammonium phosphate ester group.

5. A terpolymer according to claim 2 in which the zwitterionic monomer has the formula

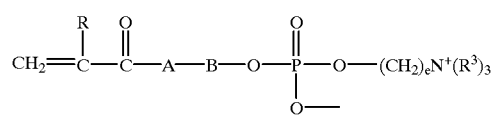

VI wherein the groups $R^3$ are the same or different and each is selected from the group consisting of hydrogen, $C_{1-24}$ alkyl, aryl, alkaryl and aralkyl groups, or two or three of the groups $R^3$ together with the nitrogen atom to which they are attached form a saturated or unsaturated heterocyclic ring; and e is 1 to 6.

6. A terpolymer according to claim 1 in which B² and Q² together represent a straight chain $C_{8-16}$-alkyl group.

7. A terpolymer according to claim 1 in which Q¹ is selected from the group consisting of $N^+R^6{}_3$, $P^+R^6{}_3$ and $S^+R^5_2$ in which the groups $R^5$ are the same or different and are each selected from the group consisting of hydrogen, $C_{1-4}$ alkyl and aryl group.

8. A terpolymer according to claim 7 in which $Q^1$ is $N^+(CH_3)_3$.

9. A terpolymer according to claim 1 in which the monomers additionally include a crosslinkable comonomer of the formula IV $$Y^3B^3Q^3 \qquad \qquad IV$$

wherein $B^3$ is selected from the group consisting of a bond, straight and branched alkylene, alkylene-oxa-alkylene and alkylene-oligooxa-alkylene groups, any of which optionally includes one or more fluorine substituents;

$Y^3$ is an ethylenically unsaturated polymerisable group; and $Q^3$ is an organic group having a reactive group capable, on imposition of an external stimulus, of reacting with a coreactive group on the surface of a substrate or which is pendant on the polymer.

10. A quater polymer having an overall cationic change formed from ethylenically unsaturated monomers including
   a) a zwitterionic monomer of the formula I $$YBX \qquad \qquad I$$

wherein
   B is selected from the group consisting of a bond, and a straight and branched alkylene, alkylene-oxa-alkylene, and alkyleneoligooxa alkylene group any of which optionally includes one or more fluorine substituents
   X is an organic group having a zwitterionic moiety; and
   Y is ethylenically unsaturated polymerisable group;
   b) a cationic monomer of the formula II $$Y^1B^1Q^1 \qquad \qquad II$$

wherein
   $B^1$ is selected from the group consisting of a bonds, and a straight and branched alkylene, alkylene-oxa-alkylene and alkylene-oligooxa-alkylene groups, any of which optionally includes one or more fluorine substituents;
   $Y^1$ is an ethylenically unsaturated polymerisable group; and
   Q is an organic group having a cationic moiety;
   c) a crosslinkable comonomer of the formula IV $$Y^3B^3Q^3 \qquad \qquad IV$$

wherein
   $B^3$ is selected from the group consisting of a bond, and a straight and branched alkylene, alkylene-oxa-alkylene and alkylene-oligooxa-alkylene groups, any of which optionally includes one or more fluorine substituents;
   $Y^3$ is an ethylenically unsaturated polymerisable group; and
   $Q^3$ is an organic group comprising a trialkyoxysilyl group; and
   d) a coreactive comonomer of the formula IV'

$$Y^{3'}B^{3'}Q^{3'} \qquad \qquad IV'$$

wherein
   $B^{3'}$ is selected from the group consisting of a bond, and straight and branched alkylene, alkylene-oxa-alkylene and alkylene-oligooxa-alkylene group, any of which optionally includes one or more fluorine substituents;
   $Y^{3'}$ is an ethylenically unsaturated polymerisable group; and
   $Q^{3'}$ is a hydroxyl group.

11. A polymerisation process in which monomers of the formula I, II and III are mixed together and radical polymerisation is initiated whereby a polymer is formed:
   a) a zwittionic monomer of the formula I $$YBX \qquad \qquad I$$

wherein
   B is selected from the group consisting of a bond, and straight and branched alkylene, alkylene-oxa-alkylene, and alkyleneoligooxa-alkylene groups any of which optionally includes one or more fluorine substituents
   X is an organic group having a zwitterionic moiety; and
   Y is ethylenically unsaturated polymerisable group;
   b) a cationic monomer of the formula II:

$$Y^1B^1Q^1 \qquad \qquad II$$

wherein
   $B^1$ is selected from the group consisting of a bond, and straight and branched alkylene, alkylene-oxa-alkylene and alkylene-oligooxa-alkylene groups, any of which optionally includes one or more fluorine substituents;
   $Y^1$ is an ethylenically unsaturated polymerisable group; and
   Q is an organic group having a cationic moiety; and
   c) in a minimum amount of about 30 mole %, a termonomer of the formula III:

$$Y^2B^2Q^2 \qquad \qquad III$$

wherein
   $Y^2$ is an ethylenically unsaturated polymerisable group; and
   $B^2$ and $Q^2$ together represent a $C_{6-24}$-alkyl group.

12. A polymerisation process in which monomers of the formula II, IV and IV' are mixed together and radical polymerisation is initiated whereby a polymer is formed:
   a) a zwitterionic monomer of the formula I $$YBX \qquad \qquad I$$

wherein
   B is selected from the group consisting of a bond, and a straight and branched alkylene, alkylene-oxa-alkylene, and alkyleneoligooxa-alkylene group any of which optionally includes one or more fluorine substituents
   X is an organic group having a zwitterionic moiety; and
   Y is ethylenically unsaturated polymerisable group;
   b) a cationic monomer of the formula II $$Y^1B^1Q^1 \qquad \qquad II$$

wherein
   $B^1$ is selected from the group consisting of a bond, and a straight and branched alkylene, alkylene-oxa-alkylene and alkylene-oligooxa-alkylene groups, any of which optionally includes one or more fluorine substituents;

$Y^1$ is an ethylenically unsaturated polymerisable group; and

Q is an organic group having a cationic moiety;

c) a crosslinkable comonomer of the formula IV $$Y^3B^3Q^3 \qquad \qquad IV$$

wherein $B^3$ is selected from the group consisting of a bond, and a straight and branched alkylene, alkylene-oxa-alkylene and alkylene-oligooxa-alkylene groups, any of which optionally includes one or more fluorine substituents;

$Y^3$ is an ethylenically unsaturated polymerisable group; and $Q^3$ is an organic group comprising a trialkyoxysilyl group; and d) a coreactive comonomer of the formula IV'

$$Y^{3'}B^{3'}Q^{3'} \qquad \qquad IV'$$

wherein $B^{3'}$ is selected from the group consisting of a bond, and straight and branched alkylene, alkylene-oxa-alkylene and alkylene-oligooxa-alkylene group, any of which optionally includes one or more fluorine substituents;

$Y^{3'}$ is an ethylenically unsaturated polymerisable group; and $Q^{3'}$ is a hydroxyl group.

13. A liquid monomer formulation comprising monomers of the general formula I, II and III:

a) a zwitterionic monomer of the formula I $$YBX \qquad \qquad I$$

wherein

B is selected from the group consisting of a bond, and straight and branched alkylene, alkylene-oxa-alkylene, and alkyleneoligooxa-alkylene groups any of which optionally includes one or more fluorine substituents X is an organic group having a zwitterionic moiety; and Y is ethylenically unsaturated polymerisable group;

b) a cationic monomer of the formula II $$Y^1B^1Q^1 \qquad \qquad II$$

wherein $B^1$ is selected from the group consisting of a bond, and a straight and branched alkylene, alkylene-oxa-alkylene and alkylene-oligooxa-alkylene groups, any of which optionally includes one or more fluorine substituents;

$Y^1$ is an ethylenically unsaturated polymerisable group; and

Q is an organic group having a cationic moiety; and c) in at least a minimum amount of about 30 mole %, a termonomer of the formula III $$Y^2B^2Q^2 \qquad \qquad III$$

wherein $Y^2$ is an ethylenically unsaturated polymerisable group; and $B^2$ and $Q^2$ together represent a $C_{6-24}$-alkyl group.

14. A liquid monomer formulation comprising monomers of the general formulae I, II, IV and IV':

a) a zwitterionic monomer of the formula I $$YBX \qquad \qquad I$$

wherein

B is selected from the group consisting of a bond, and a straight and branched alkylene, alkylene-oxa-alkylene, and alkyleneoligooxa-alkylene group any of which optionally includes one or more fluorine substituents X is an organic group having a zwitterionic moiety; and Y is ethylenically unsaturated polymerisable group;

b) a cationic monomer of the formula II $$Y^1B^1Q^1 \qquad \qquad I$$

wherein $B^1$ is selected from the group consisting of a bond, and a straight and branched alkylene, alkylene-oxa-alkylene and alkylene-oligooxa-alkylene groups, any of which optionally includes one or more fluorine substituents;

$Y^1$ is an ethylenically unsaturated polymerisable group; and

Q is an organic group having a cationic moiety;

c) a crosslinkable comonomer of the formula IV $$Y^3B^3Q^3 \qquad \qquad IV$$

wherein $B^3$ is selected from the group consisting of a bond, and a straight and branched alkylene, alkylene-oxa-alkylene and alkylene-oligooxa-alkylene groups, any of which optionally includes one or more fluorine substituents;

$Y^3$ is an ethylenically unsaturated polymerisable group; and $Q^3$ is an organic group comprising a trialkyoxysilyl group; and d) a coreactive comonomer of the formula IV'

$$Y^{3'}B^{3'}Q^{3'} \qquad \qquad IV$$

wherein $B^{3'}$ is selected from the group consisting of a bond, and straight and branched alkylene, alkylene-oxa-alkylene and alkylene-oligooxa-alkylene group, any of which optionally includes one or more fluorine substituents;

$Y^{3'}$ is an ethylenically unsaturated polymerisable group; and $Q^{3'}$ is a hydroxyl group.

15. A liquid coating composition containing a polymer according to claims 1 suspended or dissolved in a solvent.

16. A liquid coating composition containing a polymer suspended or dissolved in a solvent, further comprising an anionic mucopolysaccharide, wherein the polymer is a terpolymer having an overall cationic charge formed from ethylenically unsaturated monomers including a) a zwitterionic monomer of the formula I $$YBX \qquad \qquad I$$

wherein

B is selected from the group consisting of a bond, and straight and branched alkylene, alkylene-oxa-alkylene, and alkyleneoligooxa-alkylene groups any of which optionally includes one or more fluorine substituents X is an organic group having a zwitterionic moiety; and Y is ethylenically unsaturated polymerisable group;

b) a cationic monomer of the formula II $$Y^1B^1Q^1 \qquad \qquad II$$

wherein $B^1$ is selected from the group consisting of a bond, and straight and branched alkylene, alkylene-oxa-alkylene and alkylene-oligooxa-alkylene groups, any of which optionally includes one or more fluorine substituents;

Y is an ethylenically unsaturated polymerisable group; and

Q is an organic group having a cationic moiety; and c) a termonomer of the formula III $$Y^2B^2Q^2 \qquad \qquad III$$

wherein $B^2$ is selected from the group consisting of a bond, and straight and branched alkylene, alkylene-oxa-alkylene and alkylene-oligooxa-alkylene groups, any of which may optionally include one or more fluorine substituents;

$Y^2$ is an ethylenically unsaturated polymerisable group; and $Q^2$ is an organic group having a hydrophobic group selected from the group consisting of alkyl groups having at least six carbon atoms, fluorine substituted alkyl groups and alkyl groups having at least one siloxane substituent.

17. A coating process in which the surface of a substrate is coated with a composition according to claim 15 and the solvent is removed.

18. A coating process in which the surface of a substrate is coated with a composition containing a terpolymer according to claim 9 suspended or dissolved in a solvent, inter and/or intramolecular crosslinking or reaction with the surface is initiated, and the solvent is removed.

19. A process in which the surface of a substrate is coated with a liquid coating composition and the solvent is removed, in which the coated substrate is subsequently contacted with a solution having suspended or dissolved therein an anionically charged mucopolysaccharide, wherein the liquid coating composition contains, suspended or dissolved in a solvent, a terpolymer having an overall cationic charge formed from ethylenically unsaturated monomers including a) a zwitterionic monomer of the formula I $$YBX \qquad \qquad I$$

wherein

B is selected from the group consisting of a bond, and straight and branched alkylene, alkylene-oxa-alkylene, and alkyleneoligooxa-alkylene groups any of which optionally includes one or more fluorine substituents X is an organic group having a zwitterionic moiety; and Y is ethylenically unsaturated polymerisable group;

b) a cationic monomer of the formula II $$Y^1B^1Q^1 \qquad \qquad II$$

wherein $B^1$ is selected from the group consisting of a bond, and straight and branched alkylene, alkylene-oxa-alkylene and alkylene-oligooxa-alkylene groups, any of which optionally includes one or more fluorine substituents;

$Y^1$ is an ethylenically unsaturated polymerisable group; and

Q is an organic group having a cationic moiety, and c) a termonomer of the formula III $$Y^2B^2Q^2 \qquad \qquad III$$

wherein $B^2$ is selected from the group consisting of a bond, and straight and branched alkylene, alkylene-oxa-alkylene and alkylene-oligooxa-alkylene groups, any of which may optionally include one or more fluorine substituents;

$Y^2$ is an ethylenically unsaturated polymerisable group; and $Q^2$ is an organic group having a hydrophobic group selected from the Group consisting of alkyl groups having at least six carbon atoms, fluorine substituted alkyl groups and alkyl groups having at least one siloxane substituent.

20. A process according to claim 19 in which the anionic mucopolysaccharide is selected from heparin, hyaluronic acid, chondroitin sulphate, hirudin and an alginate.

21. A coating process in which the surface of a substrate is coated with a composition containing a polymer according to claim 10, dissolved or suspended in a solvent, inter- and/or intra-molecular cross-linking is inititated, and the solvent is removed.

22. A coating process according to claim 18, in which the coated substrate is subsequently contacted with a solution having suspended or dissolved therein an anionically charged mucopolysaccharide.

23. A coating process according to claim 21, in which the coated substrate is subsequently contacted with a solution having suspended or dissolved therein an anionically charged mucopolysaccharide.

24. A coating process according to claim 22, in which the anionic mucopolysaccharide is selected from heparin, hyaluronic acid, chondroitin sulphate, hirudin and an alginate.

25. A coating processing according claim 23, in which the anionic mucopolysaccharide is selected from heparin, hyaluronic acid, chondroitin sulphate, hirudin and an alginate.

* * * * *